United States Patent
Malatek et al.

(10) Patent No.: US 10,682,578 B1
(45) Date of Patent: Jun. 16, 2020

(54) RIDE VEHICLE RESTRAINT SYSTEM

(71) Applicant: Universal City Studios LLC, Universal City, CA (US)

(72) Inventors: Garrett Malatek, Orlando, FL (US); Rachel Wilcox, Orlando, FL (US)

(73) Assignee: Universal City Studios LLC, Universal City, CA (US)

( * ) Notice: Subject to any disclaimer, the term of this patent is extended or adjusted under 35 U.S.C. 154(b) by 0 days.

(21) Appl. No.: 16/432,709

(22) Filed: Jun. 5, 2019

Related U.S. Application Data

(60) Provisional application No. 62/780,060, filed on Dec. 14, 2018.

(51) Int. Cl.
| | |
|---|---|
| *A63G 31/12* | (2006.01) |
| *B60R 22/14* | (2006.01) |
| *B60R 21/18* | (2006.01) |
| *B60R 21/26* | (2011.01) |
| *A63G 4/00* | (2006.01) |
| *A61B 5/024* | (2006.01) |
| *B60R 21/01* | (2006.01) |

(52) U.S. Cl.
CPC .............. *A63G 31/12* (2013.01); *A61B 5/024* (2013.01); *A63G 4/00* (2013.01); *B60R 21/01* (2013.01); *B60R 21/18* (2013.01); *B60R 21/26* (2013.01); *B60R 22/14* (2013.01); *A61B 2503/12* (2013.01); *B60R 2021/01211* (2013.01)

(58) Field of Classification Search
CPC ....... A61M 21/00; A61M 21/02; A63G 31/00; A63G 31/16
USPC .......................... 472/43, 59–60, 130; 600/27
See application file for complete search history.

(56) References Cited

U.S. PATENT DOCUMENTS

| | | | | |
|---|---|---|---|---|
| 6,224,491 B1 * | 5/2001 | Hiromi | ................ | A63G 31/007 |
| | | | | 472/59 |
| 6,237,945 B1 | 5/2001 | Aboud et al. | | |
| 6,422,941 B1 | 7/2002 | Thorner et al. | | |
| 6,744,370 B1 | 6/2004 | Sleichter, III et al. | | |
| 7,691,002 B2 * | 4/2010 | Casey | ...................... | A63G 4/00 |
| | | | | 472/55 |
| 7,806,070 B2 * | 10/2010 | Williams | ............. | B60Q 1/0035 |
| | | | | 116/35 R |

(Continued)

FOREIGN PATENT DOCUMENTS

GB     2182844     5/1987

OTHER PUBLICATIONS

PCT/US2019/065174 International Search Report and Written Opinion dated Feb. 28, 2020.

*Primary Examiner* — Kien T Nguyen
(74) *Attorney, Agent, or Firm* — Fletcher Yoder, P.C.

(57) ABSTRACT

A restraint system for a ride vehicle includes a soft restraint configured to extend across a passenger to secure the passenger within a seat of the ride vehicle. The soft restraint includes a pliable material configured to conform to a substantial portion of a torso of the passenger, and a sensory stimulation system integrated with the soft restraint. The sensory stimulation system is configured to generate sensory effects and impart the sensory forces to the torso of the passenger. The soft restraint also includes an inflatable bladder system integrated with the soft restraint and the inflatable bladder system is configured to inflate with a gas to increase contact between the soft restraint and the torso of the passenger.

20 Claims, 6 Drawing Sheets

(56) References Cited

U.S. PATENT DOCUMENTS

| | | |
|---|---|---|
| 7,987,793 B2 | 8/2011 | Blonk et al. |
| 8,241,133 B1 * | 8/2012 | Lewis .................... A63G 31/16 104/53 |
| 10,059,228 B1 | 8/2018 | Aikin et al. |
| 2004/0032157 A1 | 2/2004 | Trimborn |
| 2013/0123570 A1 | 5/2013 | Ly et al. |
| 2015/0175172 A1 | 6/2015 | Truong |

* cited by examiner

RIDE VEHICLE RESTRAINT SYSTEM

CROSS-REFERENCE TO RELATED APPLICATIONS

This application claims priority from and the benefit of U.S. Provisional Application Ser. No. 62/780,060, entitled "RIDE VEHICLE RESTRAINT SYSTEM," filed Dec. 14, 2018, which is hereby incorporated by reference in its entirety.

BACKGROUND

The present disclosure relates generally to amusement park-style rides and, more specifically, to systems for securing passengers inside a ride vehicle of the amusement park-style rides.

Many amusement park-style rides include ride vehicles that carry passengers along a ride path, such as a track. As the ride vehicle travels along the ride path, the ride vehicle may be subjected to a variety of ride path features, such as turns, loops, twists, and so forth, that are part of the ride path. Indeed, the motion or movement of the ride vehicle is affected by the ride path features. As the movement of the ride vehicle changes, the passengers inside the ride vehicle may be subjected to various forces. Accordingly, ride vehicles typically include a restraint system to secure passengers within the ride vehicle as the ride vehicle travels along the ride path.

It is common for ride vehicles and amusement park-style attractions to include other features that enhance the ride vehicle experience for passengers. For example, ride vehicles, ride paths, and/or other elements of the ride system may include lights, speakers, interactive elements, specialized environments, and/or other features that provide sensory stimulation for the passenger in the ride vehicle to enhance the ride experience. It will be appreciated that passengers enjoying the ride vehicle experience may have widely varying shapes and sizes. It is now recognized that existing ride vehicle features may not provide comparable sensory stimulation for passengers of varying body geometries or proportions and/or that certain sensory stimulation systems in amusement park-style rides may be limited in their effects on some or all passengers.

BRIEF DESCRIPTION

Certain embodiments commensurate in scope with the originally claimed subject matter are summarized below. These embodiments are not intended to limit the scope of the claimed subject matter, but rather these embodiments are intended only to provide a brief summary of possible forms of the subject matter. Indeed, the subject matter may encompass a variety of forms that may be similar to or different from the embodiments set forth below.

In an embodiment, a restraint system for a ride vehicle includes a soft restraint configured to extend across a passenger to secure the passenger within a seat of the ride vehicle. The soft restraint includes a pliable material configured to conform to a substantial portion of a torso of the passenger. The soft restraint also includes a sensory stimulation system integrated with the soft restraint. The sensory stimulation system is configured to generate sensory effects and impart the sensory effects to the torso of the passenger. The soft restraint further includes an inflatable bladder system integrated with the soft restraint, which is configured to inflate with a gas to increase contact between the soft restraint and the torso of the passenger.

In an embodiment, a method for operating a ride system includes securing a passenger within a seat of a ride vehicle with a rigid restraint of the ride vehicle and applying a soft restraint that is coupled to the rigid restraint to a torso of the passenger. The method also includes inflating an inflatable bladder of an inflatable bladder system integrated with the soft restraint to increase contact between the soft restraint and the torso of the passenger. The method further includes generating a sensory effect with a sensory stimulation system integrated with the soft restraint and imparting the sensory effect to the torso of the passenger.

In an embodiment, a ride vehicle system includes a ride vehicle having a seat configured to accommodate a passenger and having a restraint system. The restraint system includes a rigid restraint configured to secure the passenger within the seat and a soft restraint coupled to the rigid restraint. The soft restraint includes a pliable material configured extend across and conform to a torso of the passenger. The restraint system further includes a sensory stimulation system integrated with the soft restraint that is configured to generate sensory effects and impart the sensory effects to the torso of the passenger. The restraint system also includes an inflatable bladder system disposed within an internal volume of the soft restraint. The inflatable bladder system is configured to inflate with a gas to bias a component of the sensory stimulation system against the torso of the passenger. The ride vehicle system further includes a controller configured to regulate operation of the sensory stimulation system, the inflatable bladder system, or both, based on sensor feedback associated with the passenger, the ride vehicle, the sensory stimulation system, the inflatable bladder system, or a combination thereof.

DRAWINGS

These and other features, aspects, and advantages of the present disclosure will become better understood when the following detailed description is read with reference to the accompanying drawings in which like characters represent like parts throughout the drawings, wherein.

Figure 5:
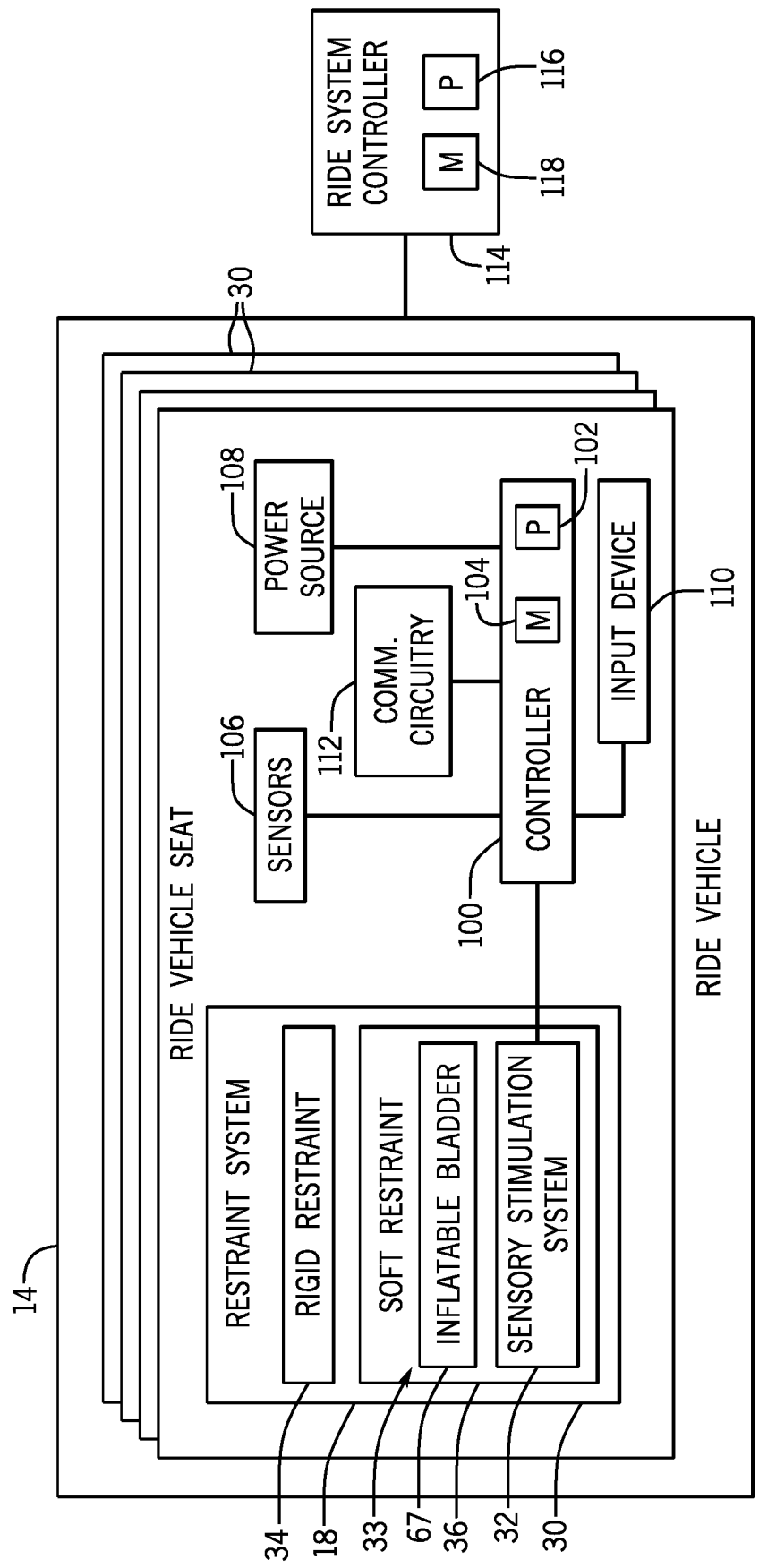
Figure 6:
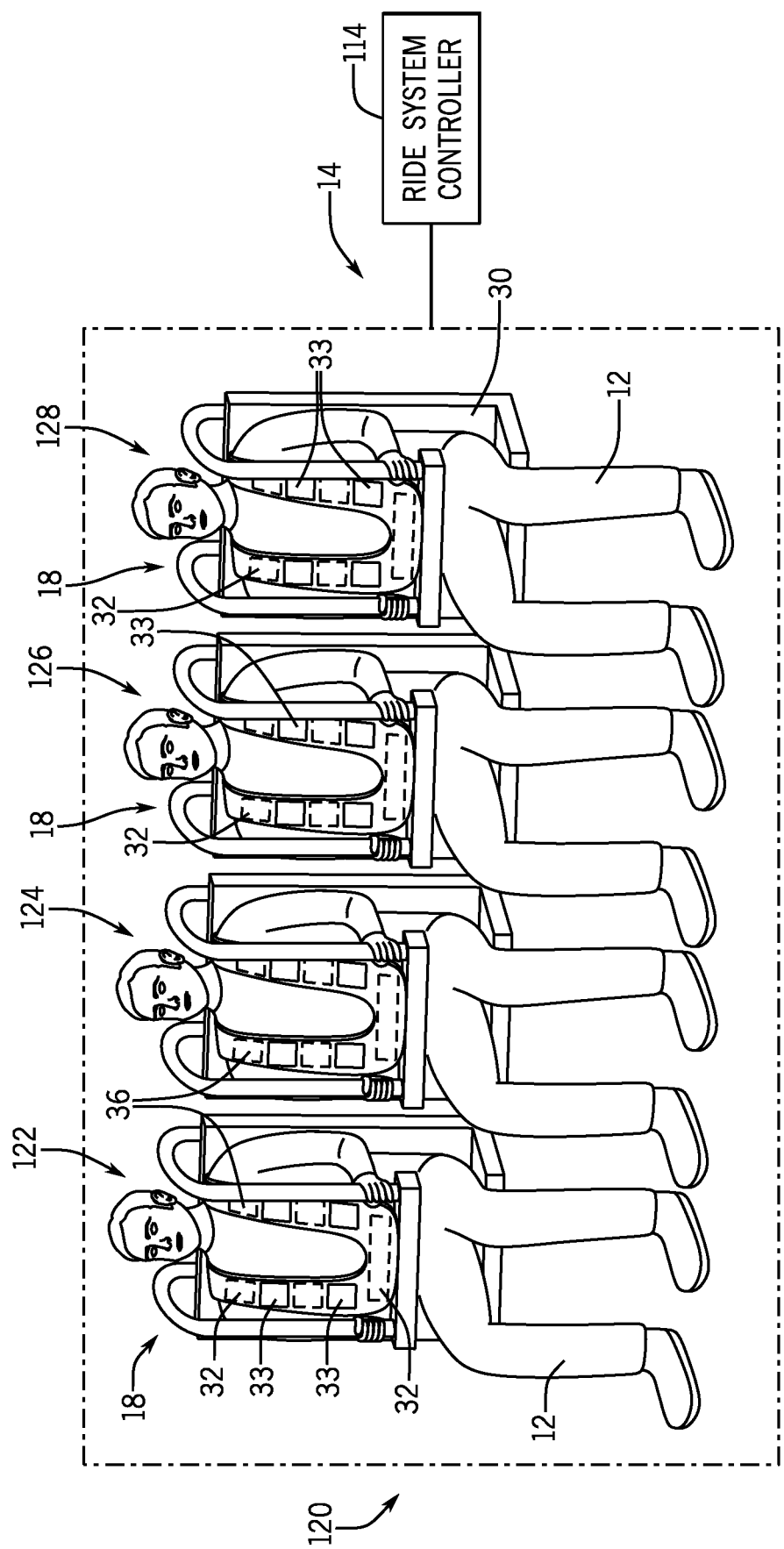

FIG. 5 is a schematic of an embodiment of a ride system, illustrating components of a ride vehicle seat of a ride vehicle, in accordance with aspects of the present disclosure; and FIG. 6 is a perspective view of an embodiment of a portion of a ride vehicle, illustrating multiple ride vehicle seats having separate restraint systems with sensory stimulation systems and inflatable bladder systems, in accordance with aspects of the present disclosure.

DETAILED DESCRIPTION

Reference will now be made in detail to specific embodiments illustrated in the accompanying drawings and figures. In the following detailed description, numerous specific details are set forth in order to provide a thorough understanding of the disclosure. However, it will be apparent to one of ordinary skill in the art that embodiments may be practiced without these specific details. In other instances, well-known methods, procedures, components, have not been described in detail so as not to unnecessarily obscure aspects of the embodiments.

It will also be understood that, although the terms first, second, etc. may be used herein to describe various elements, these elements should not be limited by these terms. These terms are only used to distinguish one element from another. For example, a first object could be termed a second object, and, similarly, a second object could be termed a first object, without departing from the scope of the present disclosure.

The terminology used herein is for the purpose of describing particular embodiments only and is not intended to be limiting. As used in the description and the appended claims, the singular forms "a," "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises" and/or "comprising," when used in this specification, specify the presence of stated features, integers, steps, operations, elements, and/or components, but do not preclude the presence or addition of one or more other features, integers, operations, elements, components, and/or groups thereof. Further, as used herein, the term "if" may be construed to mean "when" or "upon" or "in response to determining" or "in response to detecting," depending on the context.

Amusement parks include many rides that provide unique and entertaining experiences for patrons or guests. Amusement parks typically include a wide variety of rides to accommodate the thrill sensitivities and immersive experience desires of different guests. In many instances, amusement park rides include one or more ride vehicles that follow a ride path, such as a track, through a series of features. Such features may include loops, twists, turns, drops, tunnels, and so forth. The ride vehicles may travel along the ride path at high speeds and may traverse along multiple non-linear paths. As a result, passengers riding inside the ride vehicles may experience forces that may move the passengers within the ride vehicle if not otherwise restrained. Accordingly, ride vehicles frequently include restraint systems configured to secure a passenger within the ride vehicle while the ride vehicle is operating and throughout a duration of the ride experience. As will be appreciated, passengers of vastly different sizes, shapes, and proportions, such as a tall adult and a small child, may wish to enjoy the same ride experience. Accordingly, it is desirable for the ride vehicle to include restraint systems that accommodate passengers of a wide variety of body types, shapes, and sizes.

Amusement park rides also frequently include other features, such as special effects, configured to provide a more immersive and thrilling experience for the passengers on the amusement park ride. For example, amusement park rides, including ride vehicles, ride vehicle seats, and environments along the ride path, may include a variety of sensory stimulation systems. These systems can include light emitting devices, sound emitting devices, vibrational systems, thermal systems, liquid (e.g., water) spray systems, or other systems configured to stimulate one or more senses of the ride passengers. In certain existing systems, a ride vehicle may include a sensory stimulation system integrated into a seat of the ride vehicle. For example, a seat cushion and/or seat back of a ride vehicle seat may include a sensory stimulation system configured to output one or more force or effects beneath or behind a passenger sitting in the ride vehicle seat. However, such sensory stimulation systems may be significantly limited in their effect on the passenger sitting in the ride vehicle seat, and the effect experienced by the passengers may vary significantly based on different factors, such as body shape or size.

Accordingly, embodiments of the present disclosure are directed toward a ride vehicle restraint system having an integrated sensory stimulation system. Specifically, the disclosed restraint systems include elements that are configured to closely conform to a wide variety of body types, shapes, and sizes. In other words, the disclosed restraint systems are adaptable and adjustable in shape and contour to enable accommodation of differently-sized ride passengers. For example, the restraint system may include a rigid restraint configured to secure a passenger within the ride vehicle and a soft restraint configured to closely conform to the body of a passenger. In certain embodiments, the soft restraint is configured to tailor to a large or substantial portion of a passenger's torso. The soft restraint may also include an integrated inflatable bladder system configured to further promote close conformity of the soft restraint, and thus the sensory stimulation system, to the body of the passenger. In this manner, sensory stimulation of the passenger via the sensory stimulation system may be significantly enhanced. Indeed, the improved contact between the sensory stimulation system and the ride passenger via the soft restraint having the integrated inflatable bladder enables the use of various types of stimulation effects across a wide range of intensities and amounts and across a wide range of body areas (e.g., shoulder, chest, torso, ribs, waist, stomach, and so forth) of the ride passenger.

Figure 1:
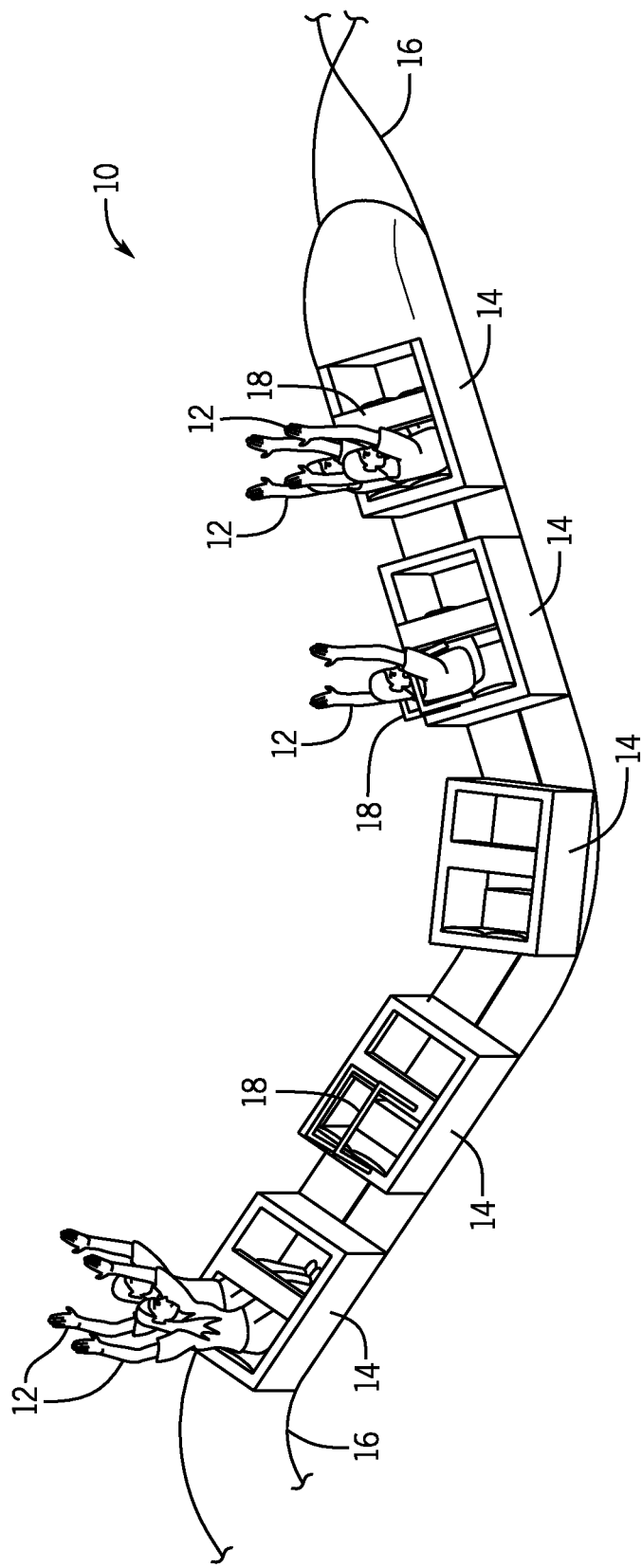
FIG. 1 is a perspective view of an embodiment of a ride system, in accordance with aspects of the present disclosure.

Turning now to the drawings, FIG. 1 is a perspective view of an embodiment of a ride system 10. The ride system 10 may include one or more ride vehicles 14 that hold one or more passengers 12. In an embodiment, multiple ride vehicles 14 may be coupled together (e.g., by a linkage). The ride vehicle 14 travels along a ride path 16 during operation of the ride system 10. The ride path 16 may be any surface on which the ride vehicle 14 travels. For example, the ride path 16 may be defined by a track. The ride path 16 may or may not dictate the path traveled by the ride vehicle 14. In an embodiment, the ride path 16 may control the movement (e.g., direction, speed, and/or orientation) of the ride vehicle 14 as it progresses along the ride path 16, similar to a train on train tracks. In another embodiment, another system may control the path taken by the ride vehicle 14 during operation of the ride system 10. For example, the ride path 16 may be an open surface that allows the passengers 12 to control certain aspects of the movement of the ride vehicle 14 via an interface system of the ride vehicle 14.

The ride vehicles 14 may accommodate any suitable number of the passengers 12. For example, the illustrated embodiment includes five ride vehicles 14 that may each accommodate two passengers 12. However, it should be understood that the ride system 10 may include any number of the ride vehicles 14. For example, the ride system 10 may include two, four, ten, twenty, or any other number of the ride vehicles 14, and each ride vehicle 14 may accommodate any number of the passengers 12. For example, one ride vehicle 14 may accommodate two passengers, another ride vehicle 14 may accommodate four passengers 12, an additional ride vehicle 14 may accommodate six passengers 12, and any further ride vehicles 14 may accommodate any number of the passengers 12.

As illustrated, the ride vehicles 14 also include restraint systems 18 configured to secure the passengers 12 within the ride vehicles 14. Each ride vehicle 14 includes at least one restraint system 18, although, in some embodiments, the ride system 10 may include separate restraint systems 18 for each passenger 12. In other words, in an embodiment, each ride vehicle 14 may include a number of restraint systems 18 equal to a total number of the passengers 12 that may ride in the ride vehicle 14 during the ride system 10 experience. As discussed in detail below, the restraint system 18 is adaptable and, more specifically, is configured to conform to a body, torso, or other body part of the passengers 12. Indeed, present embodiments of the restraint system 18 are configured to be adaptively tailored to any of a variety of body types, sizes, and shapes. To this end, the restraint system 18 may include a soft restraint that is configured to conform to a substantial portion of a body, such as a torso front side, of the passenger 12. As will be described below, the soft restraint may be formed from a pliable material that may be tightened or biased against the passenger 12 and may thereby adapt to fit closely against the passenger 12.

As mentioned above, the restraint system 18 also includes a sensory stimulation system and an inflatable bladder system integrated therein. For example, the sensory stimulation system and the inflatable bladder system may be integrated with the soft restraint of the restraint system 18, such that the inflatable bladder system may be inflated to promote close contact between elements of the sensory stimulation system and a substantial portion of the body of the passenger 12 when the restraint system 18 secures the passenger 12 within the ride vehicle 14. The close and extensive physical contact between the sensory stimulation system and the body of the passenger 12 enables the utilization of a vast range of sensory effects to enhance the ride system 10 experience, as discussed below.

It should be appreciated that the embodiment of the ride system 10 illustrated in FIG. 1 is a simplified representation intended to provide context and facilitate discussion of the presently disclosed techniques. Other embodiments of the ride system 10, including the ride vehicle 14, the ride path 16, the restraint system 18, and so forth may include similar and/or different elements or configurations. For example, while the illustrated embodiment depicts the ride vehicles 14 traveling along the ride path 16 that is positioned beneath the ride vehicles 14, other embodiments of the ride system 10 may include ride vehicles 14 that are suspended from the ride path 16 positioned above the ride vehicles. Additionally, while the illustrated restraint system 18 is shown as including a bar or other restraint positioned across the lap or legs of the passengers 12, other embodiments of the restraint system 18 may include additional or alternative components configured to restrain or otherwise confine the passengers 12 to the ride vehicle 14 during the ride system 10 operation.

Figure 2:
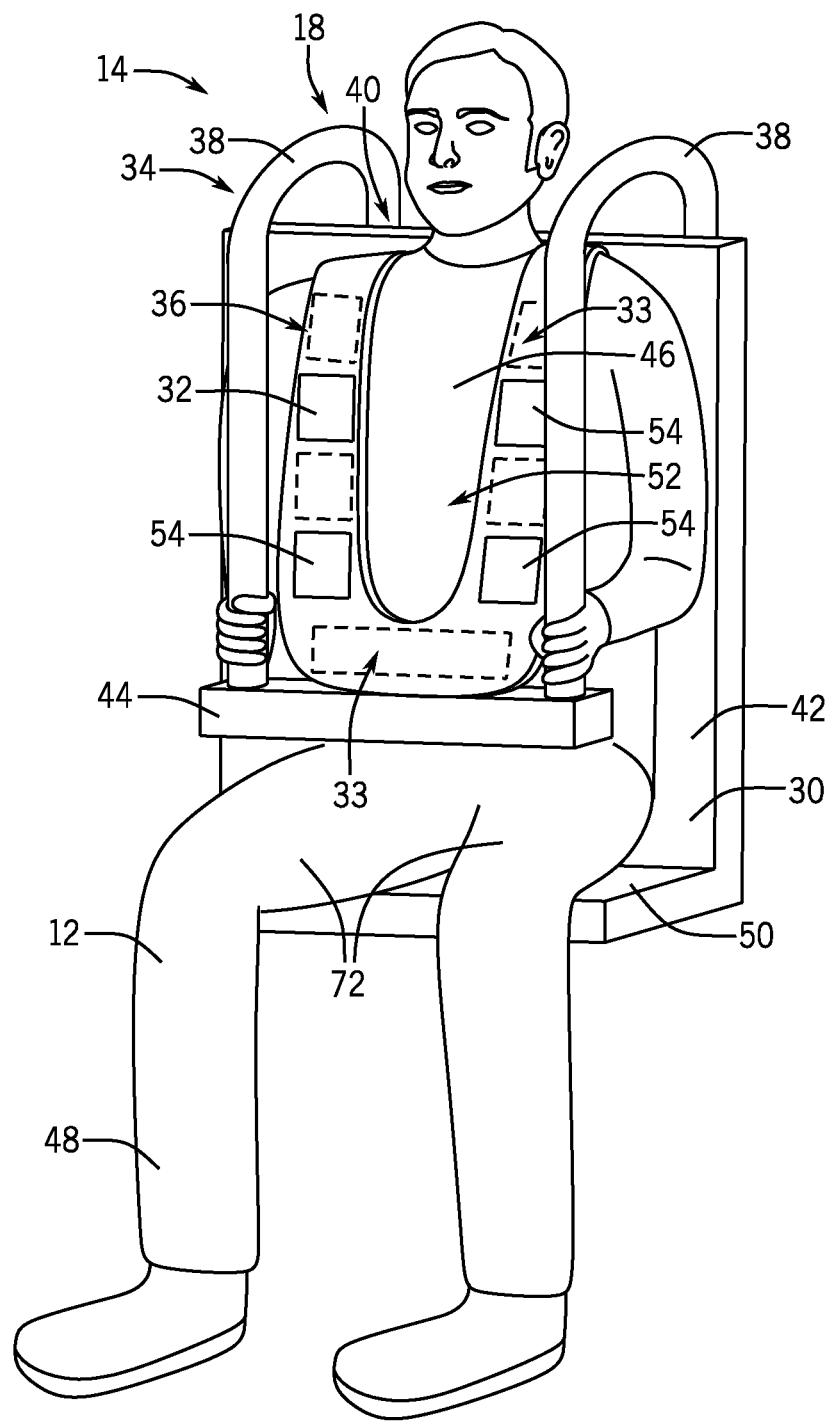
FIG. 2 is a perspective view of an embodiment of a ride vehicle seat of a ride vehicle, illustrating a sensory stimulation system and an inflatable bladder system integrated with a restraint system of the ride vehicle seat, in accordance with aspects of the present disclosure.

FIG. 2 is perspective view of an embodiment of a seat 30 of the ride vehicle 14 that may accommodate one of the passengers 12. In some embodiments, the seat 30 functions as the ride vehicle 14 and is separate from other ride vehicles 14 and/or seats 30, while in other embodiments, the seat 30 is one of multiple seats 30 within a common ride vehicle 14. As shown, the seat 30 includes an embodiment of the restraint system 18 configured to secure the passenger 12 within the seat 30 and/or within the ride vehicle 14. As shown, the restraint system 18 has a sensory stimulation system 32 (e.g., a haptic feedback system) and an inflatable bladder system 33 integrated therein, which will be discussed in further detail below.

The restraint system 18 includes a rigid restraint 34 and a soft restraint 36. The rigid restraint 34 may include components that are generally fixed, inelastic, and/or inflexible. In other words, the components of the rigid restraint 34 may generally have a fixed geometry, such as components made from metal, plastic, a composite material, or other suitably rigid material. When the restraint system 18 is in a locked or deployed configuration, the components of the rigid restraint 34 may be generally immovable and may thereby block or prevent undesirable movement of the passenger 12 within the seat 30 and/or within the ride vehicle 14.

In the illustrated embodiment, the rigid restraint 34 includes over-shoulder bars 38 that extend from a rear 40 of the seat 30, over a seat back 42 of the seat 30, and across a front side of the passenger 12 positioned in the seat 30. To enable transition of the over-shoulder bars 38 between the deployed configuration shown and a retracted configuration, the over-shoulder bars 38 may be pivotably coupled to the seat back 42, a component of the seat 30, or a component of the ride vehicle 14. The restraint system 18 may be configured to enable (e.g., via a locking system) selective rotation of the over-shoulder bars 38 relative to the seat 30. The rigid restraint 34 also includes a lap bar 44 coupled to distal ends of the over-shoulder bars 38. In the deployed configuration shown, the over-shoulder bars 38 extend over the front side of the passenger 12 to position the lap bar 44 adjacent to the legs and waist of the passenger 12. During operation of the ride system 10, the rigid restraint 34 may be locked and secured in the illustrated configuration. In this manner, the rigid restraint 34 may secure the passenger 12 within the seat 30. In particular, the over-shoulder bars 38 may retain a torso 46 of the passenger 12 substantially against the seat back 42, and the lap bar 44 may retain legs 48 of the passenger 12 substantially against a base 50 of the seat 30.

The soft restraint 36 may be formed from a pliable material configured to conform or otherwise adapt to any of a variety of body types, shapes, sizes, geometries, and/or proportions. For example, the soft restraint 36 may include a fabric, canvas, plastic, nylon, webbing, or other flexible material that may readily conform or contour to another object, such as the body of the passenger 12. In the illustrated embodiment, the soft restraint 36 has a vest-like or U-shaped configuration that is configured to be positioned over and against the torso 46 of the passenger 12 when the passenger 12 is seated in the seat 30 and/or the ride vehicle 14. However, in other embodiments, the soft restraint 36 may have other suitable configurations, such as a wrap, a sleeve, or other covering, that may cover a large surface area of the torso 46 and/or any other body part (e.g., arm, leg, hand, foot) of the passenger 12 that is not otherwise in contact with the seat 30 or the rigid restraint 34.

Furthermore, the soft restraint 36 may be sized such that the soft restraint 36 contacts a relatively large surface area of the body of the passenger 12. For example, the soft restraint 36 may be configured to cover at least 30 percent, at least 40 percent, at least 50 percent, at least 60 percent, or more, of a front side 52 of the torso 46. The torso may be generally defined as the portion of the body exclusive of the head and limbs. To enable adaptability of the soft restraint 36 for a variety of body shapes and sizes, the soft restraint 36 may be sufficiently sized to cover a substantial portion (e.g., a majority) of the front side 52 of the torso 46 of a large adult. In this way, the soft restraint 36 may contact a large surface area of the torso 46 of any or substantially any passenger 12 that may participate in the ride system 10 experience. As discussed in more detail below, certain embodiments of the restraint system 18 also have additional features, including the inflatable bladder system 33, configured to further promote contouring and/or conformity of the soft restraint 36 to the torso 46 or body of the passenger 12.

The soft restraint 36 also includes the sensory stimulation system 32 integrated therein. The sensory stimulation system 32 may include a variety of components configured to control and generate various effects, forces, elements, stimulations, or sensations for the passenger 12 secured by the soft restraint 36. For example, the sensory stimulation system 32 may include vibrational motors or actuators, thermal generators or elements, fans, aromatic elements, light emitters, controllers, power sources, sensors, or other components configured to provide the sensory sensations and to collect feedback from the passenger 12. The components may be arrayed or otherwise arranged across and throughout the soft restraint 36 to enable ample and widespread generation and transition of sensory effects from the sensory stimulation system 32 to the passenger 12 (e.g., the torso 46).

In some embodiments, components of the sensory stimulation system 32 may be packaged in one or more modules 54 that are integrated with the soft restraint 36. The modules 54 may be integrated with the material of the soft restraint 36, positioned within an interior cavity of the soft restraint 36, coupled to elements of the inflatable bladder system 33, or otherwise incorporated as an integrated element of the soft restraint 36. In an embodiment, the modules 54 and/or other components of the sensory stimulation system 32 are over-molded onto the soft restraint 36. However, it should be appreciated that, in certain embodiments, some or all components of the sensory stimulation system 32 are integrated with the soft restraint 36 without the modules 54. In other words, some or all components of the sensory stimulation system 32 may be directly integrated with the soft restraint 36 without additional packaging elements, such as a housing of the module 54.

As will be appreciated, the physical size of the soft restraint 36 enables the incorporation of multiple components (e.g., motors, actuators, sensors, etc.) of the sensory stimulation system 32 therewith. Indeed, the size of the soft restraint 36 enables the inclusion of a relatively large number of sensory output components into the sensory stimulation system 32, as compared to traditional sensory stimulation systems. As a result, the sensory stimulation system 32 is configured to generate a much wider variety of sensory effects or sensations than existing systems. For example, vibrational or tactile effects or forces generated by the sensory stimulation system 32 may vary widely in duration, intensity, amount, pattern, location on the torso 46 or body of the passenger 12, and so forth. In another embodiment, the sensory stimulation system 32 may be configured to provide complex thermal effects on particular areas of the torso 46 or body of the passenger 12. In some embodiments, the sensory effects may be generated to simulate ride vehicle 14 vibration, contact with an animal, electrical shock, recoil of a gun, an earthquake or other natural phenomenon, heat, cold, contact with water or other liquid, application of G-forces to the passenger 12, wind, among other sensations.

Figure 3:
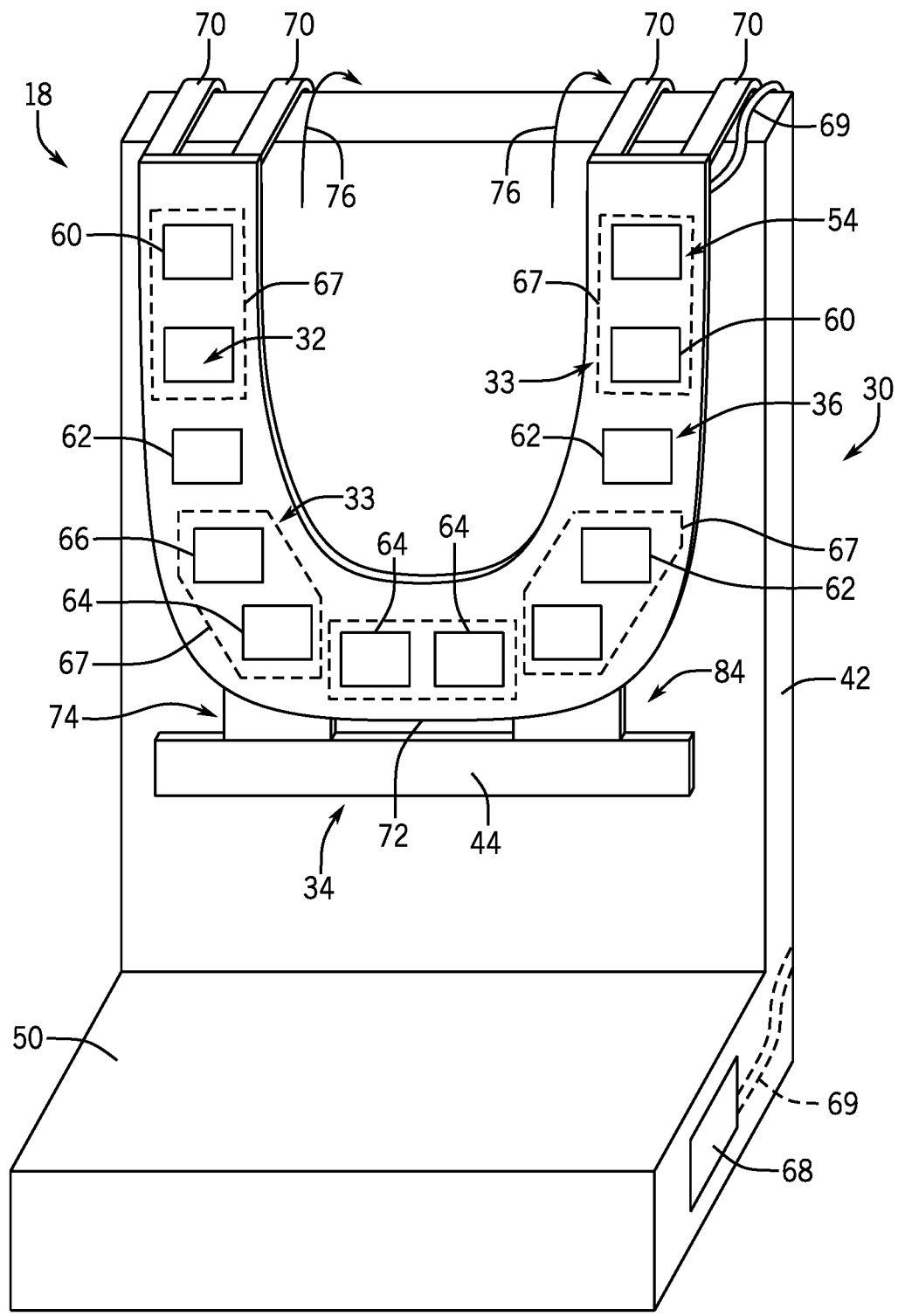
FIG. 3 is a schematic of an embodiment of a ride vehicle seat, illustrating a sensory stimulation system and an inflatable bladder system integrated with a restraint system of the ride vehicle seat, in accordance with aspects of the present disclosure.

FIG. 3 is a schematic of an embodiment of the seat 30 of the ride vehicle 14, illustrating the restraint system 18 having the sensory stimulation system 32 and the inflatable bladder system 33 integrated with the soft restraint 36. For clarity, the over-shoulder bars 38 of the rigid restraint 34 are omitted in the illustrated embodiment. As discussed above, the soft restraint 36 is configured to conform against a substantial portion (e.g., greater than 50 percent) of the body (e.g., the front side 52 of the torso 46) of the passenger 12 sitting in the seat 30. The size of the soft restraint 36 enables the inclusion of a plethora of sensory stimulation system 32 elements into the soft restraint 36, and the tailoring of the soft restraint 36, against the body of the passenger 12, enables close contact between the sensory stimulation system 32 and the passenger 12. As will further be discussed, the integration of the inflatable bladder system 33 within the soft restraint 36 promotes further improved contact between the passenger 12 and the sensory stimulation system 32 by biasing or pressing elements of the sensory stimulation system 32 against the body of the passenger 12. As a result, a wide range of sensory effects and stimulations may be utilized to enhance the ride system 10 experience for the passenger 12.

The sensory stimulation system 32 may include a variety of components configured to generate forces or effects that are experienced by the passenger 12. For example, the sensory stimulation system 32 may include actuators 60 (e.g., solenoid actuators, electrical actuators, linear resonant actuators, etc.), thermal elements 62 (e.g., electric heating elements), fans 64, motors 66 (e.g., eccentric rotating mass motors), or any other suitable element configured to generate and/or output a force or effect sensed or felt by the passenger 12. The sensory stimulation system 32 may also include other elements configured to regulate operation of the components listed above, including elements that may not be integrated with the soft restraint 36.

In addition to the sensory stimulation system 32, the inflatable bladder system 33 is also integrated with the soft restraint 36. As noted above, inflatable bladder system 33 includes elements configured to promote and enable close contact between the soft restraint 36, and thus the sensory stimulation system 32, and the passenger 12. To this end, the inflatable bladder system 33 includes one or more inflatable bladders 67 disposed in an interior volume of the soft restraint 36. More specifically, the soft restraint 36 may be a flexible covering having one or more internal volumes, pouches, or other cavities in which the inflatable bladders 67 may be disposed. Once the restraint system 18 is secured in a deployed or locked configuration with the passenger 12 in position in the seat 30, the inflatable bladders 67 may be filled with a gas, such as air, in order to achieve expansion of the inflatable bladders 67 within the soft restraint 36. As the inflatable bladders 67 expand within the volume, pouches, or cavities of the soft restraint 36, the soft restraint 36 will also expand and increase contact between the soft restraint 36, the sensory stimulation system 32, and the passenger 12. As will be appreciated, the increased contact enables improved transfer of sensory effects and forces from the sensory stimulation system 32 to the passenger 12.

In some embodiments, inflation of the inflatable bladders 67 may be achieved via a pump 68. For example, the pump 68 may be coupled to the seat 30 in the ride vehicle 14. The pump 68 may be disposed within the base 50 of the seat 30, as shown, or the pump 68 may be disposed in another suitable location, such as within a frame of the ride vehicle 14, coupled to the seat back 42 on a rear face the seat 30 (e.g., a face of the seat back 42 opposite the passenger 12), or elsewhere. A hose 69 may extend from the pump 68 to the inflatable bladders 67 disposed within the soft restraint 36 to enable transfer of gas (e.g., pressurized gas) from the pump 68 to the inflatable bladders 67. In the illustrated embodiment, the hose 69 extends from the top of the soft restraint 36, over the seat back 42, and behind the seat 30 in order to avoid interference with the passenger 12. Additional elements of the inflatable bladder system 33 (e.g., controllers, power supplies, etc.) may be incorporated into the soft restraint 36, the seat 30, and/or the ride vehicle 14 and will be discussed in further detail below.

The restraint system 18 may include other features, in addition to the inflatable bladder system 33, to further promote conformity of the soft restraint 36 to the body of the passenger 12. For example, in the illustrated embodiment, the restraint system 18 includes adjustable straps 70 coupled between the soft restraint 36 and the seat back 42 of the seat 30. The adjustable straps 70 are flexible belts that couple the soft restraint 36 to the seat 30 and enable the soft restraint 36 to be adjusted (e.g., deployed, retracted, etc.) relative to the passenger 12, such as during entry and exit of the passenger 12 from the ride vehicle 14. In an embodiment, the adjustable belts 70 are formed from webbing or other woven material.

The adjustable straps 70 may be coupled to locking retractors or other reeling mechanism coupled to the seat 30 or another portion of the ride vehicle 14. Therefore, the adjustable straps 70, which may selectively be deployed and/or retracted from the retractors, are configured to facilitate position adjustment of the soft restraint 36 relative to the passenger 12 within the seat 30. Indeed, the adjustable straps 70 may function similar to seat belts by permitting initial adjustment of the soft restraint 36 position and then locking or restricting further adjustment of the soft restraint 36 thereafter. For example, a base 72 of the soft restraint 36 may be secured to the lap bar 44 of the rigid restraint 34 (e.g., via rivets, straps, or other securement feature 74), and the adjustable straps 70 may be selectively retracted into the locking retractors once the restraint system 18 is positioned over and across the body of the passenger 12. As the adjustable straps 70 are retracted, as indicated by arrows 76, the connection between the soft restraint 36 and the lap bar 44 may become taut, and the soft restraint 36 may be pulled into closer contact with the body (e.g., torso 46) of the passenger 12. In this way, the adjustable straps 70 enable and facilitate conformity of the soft restraint 36 to the body of the passenger 12. As previously discussed, the close contact between the soft restraint 36 and the passenger 12 enables the utilization of the sensory stimulation system 32 integrated with the soft restraint 36 to generate an improved or enhanced sensory experience for the passenger 12.

Figure 4:
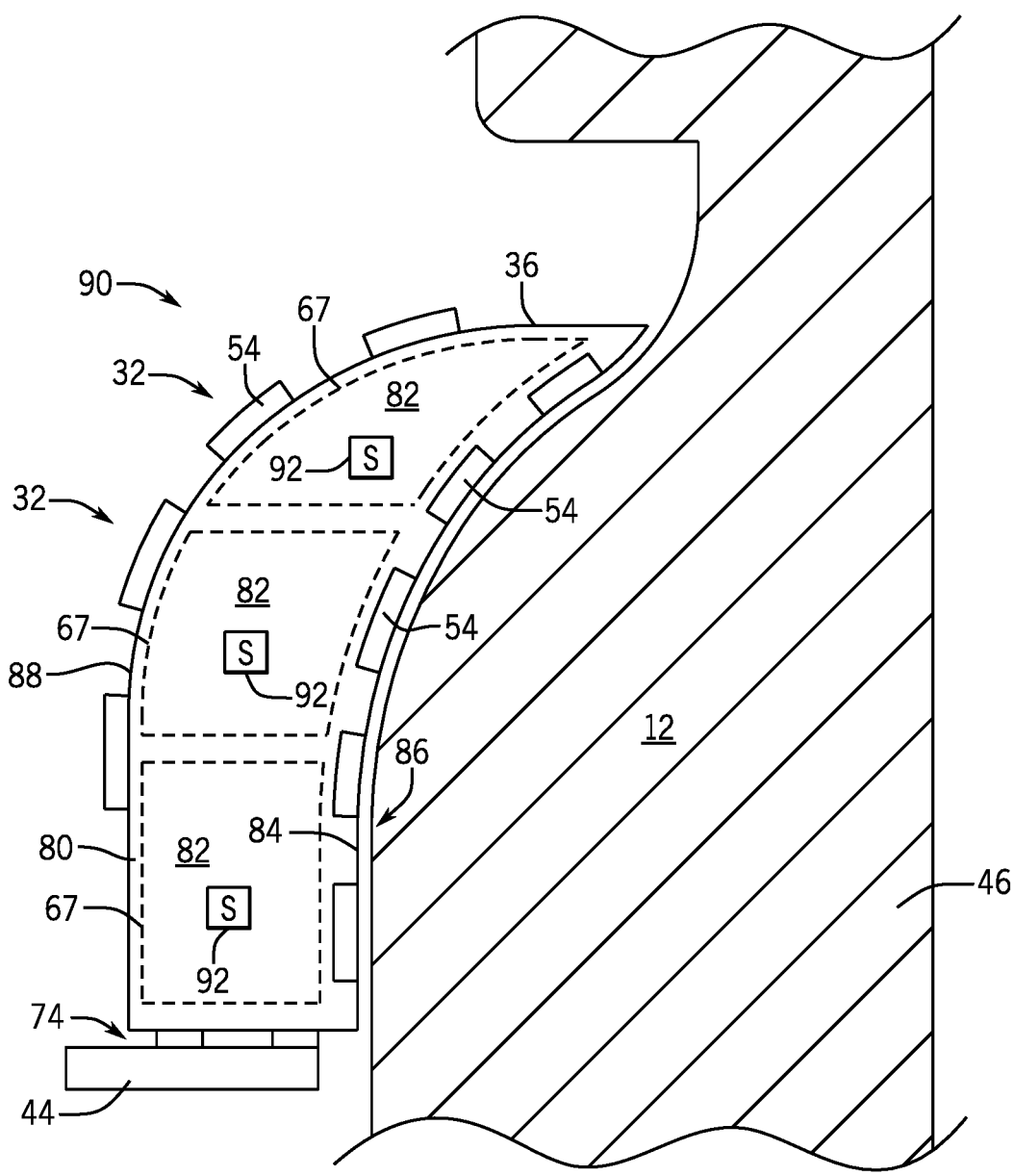
FIG. 4 is a cross-sectional side view schematic of an embodiment of a restraint system having an integrated sensory stimulation system and inflatable bladder system engaged with a ride vehicle passenger, in accordance with aspects of the present disclosure.

FIG. 4 is a cross-sectional side view schematic of the soft restraint 36 deployed against the passenger 12 with the inflatable bladder system 33 in an inflated configuration. As shown, the inflatable bladders 67 are disposed within an internal volume 80 of the soft restraint 36 and are filled with a gas 82. The illustrated embodiment shows three inflatable bladders 67, but other embodiments of the restraint system 18 may include any other suitable number of inflatable bladders 67. Each inflatable bladder 67 may be disposed in a separate volume or pouch of the soft restraint 36, or the inflatable bladders 67 may be disposed in a common volume, such as the internal volume 80. The gas 82 within the inflatable bladders 67 may be pressurized and causes the inflatable bladders 67 to expand, thereby biasing the soft restraint 36 against the torso 46 of the passenger 12. In this manner, close contact between elements of the sensory stimulation system 32 and the body of the passenger 12 may be achieved. For example, in the illustrated embodiment, the sensory stimulation system 32 includes the modules 54, each of which may include one or more elements discussed above that are configured to output a sensory force or effect. Some modules 54 are positioned on an inner surface 84 of the soft restraint 36 and on a passenger-facing side 86 of the soft restraint 36. As a result, the modules 54 are positioned between the inflatable bladders 67 and the torso 46 of the passenger 12, such that the modules 54 are captured or "sandwiched" between the inflatable bladders 67 and the passenger 12 when the inflatable bladders 67 are filled with the gas 82. With the modules 54 biased or pressed against the torso 46 of the passenger 12, the passenger 12 may more readily experience effects or forces emitted from the modules 54 (e.g., heat, vibration, air flow, etc.), including localized, faint, and/or subtle effects or forces, which may not otherwise be perceived by the passenger 12.

In some embodiments, the soft restraint 36 may include modules 54 positioned on an outer surface 88 of the soft restraint 36, including on the passenger-facing side 86 of the soft restraint 36 and/or on an outward-facing side 90 of the soft restraint 36. Indeed, the modules 54 may be positioned in any suitable location on or within the soft restraint 36 to enable a desired sensory effect for the passenger 12. As mentioned above, the sensory elements of the sensory stimulation system 32 (e.g., actuators 60, thermal elements 62, fans 64, motors 66, etc.) may be disposed on or within the soft restraint 36 without the modules 54 (e.g., a housing). In some embodiments, one or more sensory elements of the sensory stimulation system 32 may be coupled to or integrated with the inflatable bladders 67.

The soft restraint 36 may also include integrated sensors 92, which may be configured to provide feedback to a control system of the sensory stimulation system 32 and/or the inflatable bladder system 33. For example, the sensors 92 may be configured to provide feedback indicative of an operating parameter of the sensory stimulation system 32 (e.g., an intensity of a force or effect output), an operating parameter of the inflatable bladder system 33 (e.g., a pressure of the gas 82 within the inflatable bladders 67), and/or feedback related to a condition of the passenger 12 (e.g., passenger heart rate). The control system may utilize the feedback provided by the integrated sensors 92 to further regulate, refine, or otherwise control operation of the sensory stimulation system 32 and/or the inflatable bladder system 33.

FIG. 5 is a schematic of an embodiment of the ride system 10, illustrating components of the ride vehicle 14 and the seat 30 of the ride vehicle 14. As previously discussed, the seat 30 includes the restraint system 18 having the rigid restraint 34 and the soft restraint 36 with the integrated sensory stimulation system 32 and inflatable bladder system 33. The seat 30 may also include other elements that facilitate operation of the restraint system 18 and, more particularly, the sensory stimulation system 32 and inflatable bladder system 33. It should be appreciated that the components discussed below may be integrated with the soft restraint 36, other elements of the restraint system 18, the seat 30, the ride vehicle 14, or any combination thereof.

For example, the sensory stimulation system 32 may communicate with a controller 100 configured to send control signals to the force or effect-generating components and to receive feedback from the sensory stimulation system 32. Similarly, the controller 100 may communicate with the inflatable bladder system 33 to send control signals (e.g., to the pump 68) to enable operation of the inflatable bladder system 33 and to receive feedback from the inflatable bladder system 33. In some embodiments, the controller 100 is common to the sensory stimulation system 32 and the inflatable bladder system 33, but in other embodiments, multiple controllers 100 may be utilized.

The controller 100 may be integrated with the soft restraint 36, the seat 30, or another component of the ride vehicle 14. The controller 100 includes a processor 102 and a memory 104. For example, the processor 102 may be a microprocessor that executes software to control motors (e.g., high frequency motors, stepper motors) or other elements to generate sensory effects or forces in response to the location, time, current scene/image of the ride, or a combination thereof. The processor 102 may include multiple microprocessors, one or more "general-purpose" microprocessors, one or more special-purpose microprocessors, and/or one or more application specific integrated circuits (ASICs), field-programmable gate arrays (FPGAs), or some combination thereof. For example, the processor 102 may include one or more reduced instruction set (RISC) processors.

The memory 104 may include a volatile memory, such as random access memory (RAM), and/or a nonvolatile memory, such as read-only memory (ROM). The memory 104 may store a variety of information and may be used for various purposes. For example, the memory 104 may store processor executable instructions, such as firmware or software, for the processor 102 to execute. The memory 104 may include ROM, flash memory, a hard drive, or any other suitable optical, magnetic, or solid-state storage medium, or a combination thereof. The memory 104 may store data, instructions, and any other suitable data. In operation, the processor 102 executes instructions on the memory 104 to generate and/or provide control signals to components of the sensory stimulation system 32 and the inflatable bladder system 33.

As mentioned above, the sensory stimulation system 32 and/or the inflatable bladder system 33 may include one or more sensors 106, including the sensors 92 integrated with the soft restraint 36. However, other sensors 106 may be positioned elsewhere, such as within the seat 30. The sensors 106 are configured to collect feedback that may be used to further control operation of the sensory stimulation system 32 and/or the inflatable bladder system 33. For example, as mentioned above, the sensors 106 may include a heart rate sensor configured to detect or measure a heart rate of the passenger 12, and the controller 100 may utilize the heart rate feedback to adjust operation of the sensory stimulation system 32 and/or the inflatable bladder system 33. In an embodiment, if the heart rate of the passenger 12 secured by the restraint system 18 exceeds a threshold value, the controller 100 may regulate operation to reduce an intensity of forces or effects generated by the sensory stimulation system 32 or may suspend operation of the sensory stimulation system 32. The sensors 106 may also include pressure sensors (e.g., to detect the presence of the passenger 12 in the seat 30, to detect a pressure of the gas 82 within the inflatable bladders 67, etc.), temperature sensors (e.g., to detect a temperature of the passenger 12 or an environment surrounding the ride vehicle 14), position sensors (e.g., to detect a position of the ride vehicle 14 along the ride path 16) or any other suitable sensor configured to collect and provide feedback for use in regulating operation of the sensory stimulation system 32 and/or the inflatable bladder system 33.

Further, the sensory stimulation system 32 and the inflatable bladder system 33 may include one or more power sources 108, which are configured to provide electrical power to components of the sensory stimulation system 32 and the inflatable bladder system 33, such as the actuators 60, the thermal elements 62, the fans 64, the controller 100, and so forth. The power sources 108 may be integrated into the seat 30 or another portion of the ride vehicle 14 or ride system 10. For example, in one embodiment, the power source 108 is a battery positioned within the ride vehicle 14. In another embodiment, the power source 108 may be an electrical connection to another power supply external to the ride vehicle 14. For example, the power source 108 may be electrically coupled to a bus bar of the ride system 10.

The sensory stimulation system 32 and/or the inflatable bladder system 33 may also include one or more input devices 110, in some embodiments. The input device 110 is configured to receive feedback, via interaction of the passenger 12 with the input device 110, for use in further regulating operation of the sensory stimulation system 32 and/or the inflatable bladder system 33. For example, in one embodiment, the input device 110 is a button or switch that the passenger 12 may toggle to activate and deactivate the sensory stimulation system 32. In another embodiment, the input device 110 includes a dial, button, touchscreen, slider, or other component configured to enable the passenger 12 to adjust settings of the sensory stimulation system 32, such as an intensity of vibrational forces generated by the sensory stimulation system 32. In some embodiments, the input device 110 may include buttons or switches configured to enable inflation and/or deflation of the inflatable bladders 67.

As illustrated, the sensory stimulation system 32 and the inflatable bladder system 33 may also include communication circuitry 112 that enables communication with systems external to the ride vehicle 14. For example, the communication circuitry 112 may be configured to communicate with a ride system controller 114 of the ride system 10 (e.g., a central system controller), such as via a wired connection or a wireless connection. The communication circuitry 112 may communicate various types of information to the ride system controller 114 for use in regulation of the ride system 10 operation. Types of information may include a number of passengers 12 in the ride vehicle 14, an identification of occupied and unoccupied seats 30 of the ride vehicle 14, data associated with operating parameters of the sensory stimulation system 32, data associated with operating parameters of the inflatable bladder system 33, a position of the ride vehicle 14 along the ride path 16, a speed of the ride vehicle 14, a position or state of the restraint systems 18, or any other suitable information.

The ride system controller 114 includes a processor 116, which may be similar to the processor 102 discussed above, and a memory 118, which may be similar to the memory 104 discussed above. Based on information received from the communication circuitry 112, the ride system controller 114 may regulate operation of the ride system 10. For example, the ride system controller 114 may control the start time of the ride vehicle 14 experience, an end time of the ride vehicle 14 experience, the speed of the ride vehicle 14 on the ride path 16, and so forth. In some embodiments, the ride system controller 114 and the communication circuitry 112 may communicate with one another to coordinate operation of the sensory stimulation system 32 with other sensory systems of the ride system 10. For example, the ride system controller 114 and the communication circuitry 112 may coordinate operation of the sensory stimulation system 32 to generate a particular vibrational or heat pattern when the ride vehicle 14 passes a certain location along the ride path 16 and/or to coincide with the generation of a light/image display and/or sound output of the ride system 10. In an embodiment, the sensory stimulation system 32 may generate vibrational forces representative of an electrical shock and/or may activate fans 64 to simulate wind when the ride vehicle 14 is approaching a light display simulating a lightning storm. In another embodiment, the sensory stimulation system 32 may generate small, focused vibrational forces that seemingly travel or progress across the body of the passenger 12 to simulate contact with insects when the ride vehicle 14 enters a simulated jungle or grasslands environment along the ride path 16. In another embodiment, the sensory stimulation system 32 may generate heat when the ride vehicle 14 passes a simulated fire or explosion along the ride path 16.

FIG. 6 is a perspective view of an embodiment of the ride vehicle 14, illustrating multiple seats 30 having respective passengers 12 and restraint systems 18. As illustrated, each restraint system 18 includes the sensory stimulation system 32 and the inflatable bladder system 33 integrated within the soft restraint 36 of the respective restraint system 18, in accordance with present techniques.

As discussed in detail above, the sensory stimulation system 32 is configured to provide a wide range of unique sensory stimulations via the generation of forces or effects (e.g., vibration, heat, air flow, etc.) that are imparted to the passenger 12 secured by the restraint system 18. Indeed, the restraint system 18, having the integrated sensor stimulation system 32 and inflatable bladder system 33 disclosed herein, enable the generation and transmission of forces or effects that may be selected, tuned, or otherwise customized to represent or simulate any of a plethora of sensations, which may be coordinated with other aspects or sensory stimulations (e.g., lights, sounds, smells, etc.) that are part of the ride system 10 experience for the passenger 12.

While the operation of each sensory stimulation system 32 may be coordinated with other systems (e.g., sensory systems) of the ride system 10, in certain embodiments operation of the sensory stimulation system 32 may be coordinated with other sensory stimulation systems 32 within the same ride system 10. For example, the ride system controller 114 or another controller, such as a dedicated controller of the ride vehicle 14, may coordinate operation of sensory stimulation systems 32 included within a row 120 of seats 30 within the ride vehicle 14. For example, a controller may control operation of the sensory stimulation system 32 associated with a first passenger 122 to generate a particular type of vibrational force or thermal effect imparted to the first passenger 122 at a first time. Thereafter, the controller may control operation of the sensory stimulation system 32 associated with a second passenger 124 to generate the same particular type of vibrational force or thermal effect imparted to the first passenger 122. The controller may continue to regulate operation of the various sensory stimulation systems 32 within the row 120 to transition the particular vibrational or thermal sensation sequentially to a third passenger 126 and then a fourth passenger 128 to simulate an element or phenomenon (e.g., a slithering snake, a flow of hot water, an electrical shock, recoil of a gun, the spread of a fire, etc.) traveling across the passengers 12 in the row 120. In this manner, the sensory stimulation systems 32 may enhance the ride system 10 experience shared amongst the passengers 12 within the ride vehicle 14. Alternatively, at least one passenger 12 may receive a different sensory experience than others passengers 12 or may choose to not receive the sensory experience.

Accordingly, embodiments of the present disclosure are directed toward a ride vehicle restraint system having an integrated sensory stimulation system and an integrated inflatable bladder system. The disclosed restraint systems include elements, such as a soft restraint, which closely conform to a wide variety of body types, shapes, and sizes. In other words, the disclosed restraint systems are adaptable and adjustable in shape and contour to enable accommodation of differently-sized ride vehicle passengers. The sensory stimulation system and the inflatable bladder system may be integrated with the soft restraint. As the soft restraint is adjustable to closely conform to a large portion of the body of the ride passenger, the operation of the inflatable bladder system promotes placement of the sensory stimulation system in close contact with the body of the passenger and across a large surface area of the passenger's body, as compared to existing restraint systems. In this manner, sensory stimulation of the passenger may be enhanced. Indeed, the improved and increased contact between the sensory stimulation system and the passenger via the inflatable bladder system of the soft restraint enables the use of sensory stimulation (e.g., vibrations, heat, air flow, etc.) across a wide range of force or effect intensities, patterns and amounts, and across a wide range of passenger body areas.

While only certain features of the present disclosure have been illustrated and described herein, many modifications and changes will occur to those skilled in the art. It is, therefore, to be understood that the appended claims are intended to cover all such modifications and changes as fall within the true spirit of the disclosure.

The invention claimed is:

1. A restraint system for a ride vehicle, comprising:
   a soft restraint configured to extend across a passenger to secure the passenger within a seat of the ride vehicle, wherein the soft restraint comprises a pliable material configured to conform to a substantial portion of a torso of the passenger;
   an inflatable bladder system integrated with the soft restraint, wherein the inflatable bladder system is configured to inflate with a gas to increase contact between the soft restraint and the torso of the passenger, wherein the inflatable bladder system comprises an inflatable bladder disposed within an internal volume of the soft restraint; and
   a sensory stimulation system integrated with the soft restraint, wherein the sensory stimulation system is configured to generate sensory effects and impart the sensory effects to the torso of the passenger, and wherein the sensory stimulation system comprises an effect-generating element disposed between the inflatable bladder and the torso of the passenger when the soft restraint is in a deployed position.

2. The restraint system of claim 1, wherein the effect-generating element comprises a motor, a vibrational actuator, a thermal component, a fan, or any combination thereof.

3. The restraint system of claim 1, wherein the inflatable bladder system comprises a pump coupled to the inflatable bladder via a hose, and wherein the pump is configured to supply the gas to the inflatable bladder.

4. The restraint system of claim 3, wherein the pump is coupled to or disposed within the seat.

5. The restraint system of claim 1, wherein the inflatable bladder system comprises:
   a sensor configured to collect feedback associated with the passenger, the inflatable bladder system, the ride vehicle, or a combination thereof; and
   a controller configured to control adjustment of an operation of the inflatable bladder system based on the collected feedback.

6. The restraint system of claim 5, wherein the sensor comprises a heart rate sensor configured to detect a heart rate of the passenger, a pressure sensor configured to detect a pressure of the gas within the inflatable bladder of the inflatable bladder system, or both.

7. The restraint system of claim 1, comprising a rigid restraint configured to extend across the passenger to secure the passenger within the seat of the ride vehicle, wherein the soft restraint is coupled to the rigid restraint.

8. The restraint system of claim 1, comprising a plurality of straps configured to couple the soft restraint to the seat of the ride vehicle and to secure the soft restraint against the torso of the passenger.

9. The restraint system of claim 1, wherein the sensory stimulation system comprises:
a sensor configured to collect feedback associated with the passenger, the sensory stimulation system, the ride vehicle, or a combination thereof; and
a controller configured to control adjustment of an operation of the sensory stimulation system based on the collected feedback.

10. The restraint system of claim 1, comprising:
a controller configured to control adjustment of an operation of the sensory stimulation system, the inflatable bladder system, or both; and
an input device communicatively coupled to the controller, wherein the input device is configured to enable adjustment of an operation of the sensory stimulation system, the inflatable bladder system, or both, by the passenger.

11. A method for operating a ride system, comprising:
securing a passenger within a seat of a ride vehicle with a rigid restraint of the ride vehicle;
applying a soft restraint to a torso of the passenger, wherein the soft restraint is coupled to the rigid restraint;
inflating an inflatable bladder of an inflatable bladder system integrated with the soft restraint to increase contact between the soft restraint and the torso of the passenger;
biasing an effect-generating element against the torso of the passenger, wherein the effect-generating element is integrated with the soft restraint and is disposed between the inflatable bladder and the torso of the passenger;
generating a sensory effect with the effect-generating element; and
imparting the sensory effect to the torso of the passenger.

12. The method of claim 11, wherein generating the sensory effect comprises generating vibrations, heat, air flow, sound, light, or any combination thereof.

13. The method of claim 11, wherein inflating the inflatable bladder comprises filling the inflatable bladder with gas via a pump and a hose, wherein the inflatable bladder is disposed within an internal volume of the soft restraint.

14. The method of claim 11, comprising:
collecting, via a sensor, feedback associated with the passenger, the inflatable bladder system, the ride vehicle, or a combination thereof; and
adjusting operation of the inflatable bladder system based on the feedback.

15. The method of claim 11, comprising:
collecting, via a sensor, feedback associated with the passenger, the effect-generating element, the ride vehicle, or a combination thereof; and
adjusting operation of the effect-generating element based on the feedback.

16. A ride vehicle system, comprising:
a ride vehicle comprising a seat configured to accommodate a passenger;
a restraint system of the ride vehicle, wherein the restraint system comprises:
a rigid restraint configured to secure the passenger within the seat;
a soft restraint coupled to the rigid restraint, wherein the soft restraint comprises a pliable material configured extend across and conform to a torso of the passenger; and
a sensory stimulation system integrated with the soft restraint, wherein the sensory stimulation system is configured to generate sensory effects and impart the sensory effects to the torso of the passenger; and
an inflatable bladder system disposed within an internal volume of the soft restraint, wherein the inflatable bladder system is configured to inflate with a gas to bias an effect-generating component of the sensory stimulation system against the torso of the passenger; and
a controller configured to regulate operation of the sensory stimulation system, the inflatable bladder system, or both, based on sensor feedback associated with the passenger, the ride vehicle, the sensory stimulation system, the inflatable bladder system, or a combination thereof.

17. The ride vehicle system of claim 16, wherein the effect-generating component of the sensory stimulation system comprises a motor, a vibrational actuator, a thermal component, a fan, or a combination thereof.

18. The ride vehicle system of claim 16, wherein the inflatable bladder system comprises a plurality of inflatable bladders disposed within the internal volume of the soft restraint, wherein each inflatable bladder of the plurality of inflatable bladders is configured to inflate with the gas.

19. The ride vehicle system of claim 16, wherein the sensory stimulation system comprises a plurality of modules integrated with the soft restraint, wherein each module of the plurality of modules is configured to generate at least one of the sensory effects.

20. The ride vehicle system of claim 19, wherein a first module of the plurality of modules is disposed within the internal volume of the soft restraint, and wherein a second module of the plurality of modules is external to the internal volume of the soft restraint.

\* \* \* \* \*